(12) United States Patent
Swaminathan et al.

(10) Patent No.: US 12,182,482 B2
(45) Date of Patent: Dec. 31, 2024

(54) METHOD FOR PREDICTING OUTCOME OF AN MODELLING OF A PROCESS IN A BIOREACTOR

(71) Applicant: Cytiva Sweden AB, Uppsala (SE)

(72) Inventors: Krishna Kumar Swaminathan, Bangalore Karnataka (IN); Sridhar Dasaratha, Bangalore Karnataka (IN); Sittal George, Bangalore Karnataka (IN); Vinay Bhaskar Jammu, Bangalore Karnataka (IN); Alok Singh Chauhan, Bangalore Karnataka (IN); Nagaraju Konduru, Bangalore Karnataka (IN); Neelima Boddapati, Bangalore Karnataka (IN); Ankita Bhatia, Bangalore Karnataka (IN); Mithilesh Mohanty, Bangalore Karnataka (IN); Harsha Aeron, Bangalore Karnataka (IN); Andreas Castan, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 407 days.

(21) Appl. No.: 16/620,940

(22) PCT Filed: Jun. 18, 2018

(86) PCT No.: PCT/IN2018/050398
§ 371 (c)(1),
(2) Date: Dec. 10, 2019

(87) PCT Pub. No.: WO2018/229802
PCT Pub. Date: Dec. 20, 2018

(65) Prior Publication Data
US 2020/0202051 A1    Jun. 25, 2020

(30) Foreign Application Priority Data
Jun. 16, 2017 (IN) .............................. 201741021125

(51) Int. Cl.
*G06F 30/20* (2020.01)

(52) U.S. Cl.
CPC .................................... *G06F 30/20* (2020.01)

(58) Field of Classification Search
CPC ..................................................... G06F 30/20
See application file for complete search history.

(56) References Cited

U.S. PATENT DOCUMENTS

| | | | | |
|---|---|---|---|---|
| 2005/0158701 A1* | 7/2005 | West | ...................... | G05D 21/02 435/3 |
| 2005/0260743 A1* | 11/2005 | Drake | .................... | C12M 41/48 702/19 |

(Continued)

FOREIGN PATENT DOCUMENTS

| | | | | |
|---|---|---|---|---|
| CN | 101080488 A | * | 11/2007 | ............... C12N 7/00 |
| CN | 101415816 A | * | 4/2009 | ........... G01N 33/502 |

(Continued)

OTHER PUBLICATIONS

Bastin, et al.; On-line Estimation and Adaptive Control of Bioreactors; Chapter 5 'Adaptive Control of Bioreactors' (Year: 1990).*

(Continued)

*Primary Examiner* — Rehana Perveen
*Assistant Examiner* — Nupur Debnath
(74) *Attorney, Agent, or Firm* — Eversheds-Sutherland (US) LLP

(57) ABSTRACT

The present invention relates to a method for predicting outcome of a process used for manufacturing a sample in a bioreactor, the process belonging to a category. The method comprises selecting (51) a process model based on the category; accessing (53) historic data related to past process runs for manufacturing the sample; accessing (53) current data obtained (54) from a current process run of the process. The obtained current data, which is based on the selected (Continued)

process model, comprises: process strategy data, bioreactor instrument data, data from online sensors and/or data from offline sensors. The method further comprises predicting (62) an outcome of at least one selected parameter of the current process run for manufacturing the sample based on the accessed historic data and current data. The present invention also relates to a method for modelling a process and a control system (10) for controlling a process.

32 Claims, 7 Drawing Sheets

(56) References Cited

U.S. PATENT DOCUMENTS

| | | | | |
|---|---|---|---|---|
| 2008/0177518 | A1* | 7/2008 | Krishnamoorthy | G06F 30/20 703/9 |
| 2009/0048816 | A1 | 2/2009 | Srinivasa et al. | |
| 2009/0104653 | A1* | 4/2009 | Paldus | C12Q 1/06 435/39 |
| 2009/0252749 | A1* | 10/2009 | Leister | A61P 13/12 424/178.1 |
| 2010/0184147 | A1* | 7/2010 | Cheng | C12N 5/0018 435/70.1 |
| 2011/0217690 | A1* | 9/2011 | Niazi | C12Q 3/00 435/3 |
| 2012/0065782 | A1* | 3/2012 | West | G05D 21/02 700/266 |
| 2012/0107921 | A1* | 5/2012 | Willson | C12M 41/48 47/1.4 |
| 2012/0149885 | A1* | 6/2012 | Niazi | B01F 27/9212 530/413 |
| 2013/0281355 | A1* | 10/2013 | Vijayasankaran | C12P 21/00 435/325 |
| 2014/0154726 | A1* | 6/2014 | Yang | C12M 23/50 435/29 |
| 2015/0275167 | A1* | 10/2015 | Faris | A61K 9/2866 435/325 |
| 2015/0329817 | A1 | 11/2015 | Namatame et al. | |
| 2016/0122701 | A1* | 5/2016 | Higgs, III | C12M 35/04 703/2 |
| 2016/0264940 | A1* | 9/2016 | Broly | C12N 5/0037 |
| 2017/0177835 | A1* | 6/2017 | Cardoso-Menezes | G01N 21/278 |
| 2018/0101529 | A1* | 4/2018 | Karpistsenko | G06F 16/1873 |
| 2020/0071693 | A1* | 3/2020 | Sunspiral | C12N 1/14 |

FOREIGN PATENT DOCUMENTS

| | | | |
|---|---|---|---|
| CN | 102131383 A | 7/2011 | |
| CN | 103827292 A * | 5/2014 | C07K 16/00 |
| CN | 206033776 U * | 3/2017 | |
| CN | 206219583 U * | 6/2017 | |
| EP | 1598415 A1 | 11/2005 | |
| EP | 1244955 B1 | 10/2010 | |
| IN | 590DELNP2011 A | 2/2012 | |
| JP | 2003235544 A | 8/2003 | |
| JP | 2015216886 A | 12/2015 | |
| WO | 2007/038572 A2 | 4/2007 | |
| WO | 2008/140689 A2 | 11/2008 | |
| WO | WO-2010002745 A1 * | 1/2010 | A01G 7/02 |
| WO | WO-2015003012 A2 * | 1/2015 | C12M 23/40 |
| WO | 2015097217 A1 | 7/2015 | |
| WO | WO-2015188009 A1 * | 12/2015 | C07K 16/00 |
| WO | WO-2016004322 A2 * | 1/2016 | G01N 21/65 |
| WO | 2016/196315 A2 | 12/2016 | |

OTHER PUBLICATIONS

Jessica et al; "In Situ Raman Spectroscopy for Simultaneous Monitoring of Multiple Process Parameters in Mammalian Cell Culture Bioreactors"; 2012 American Institute of Chemical Engineers; (Year: 2012).*
S. Craven et al. "Modeling a mammalian cell bioprocess for different operation modes and bioreactor scales"; Biotechnol. Progr. 29 (1) (2013) 186-196. (Year: 2013).*
N.R. Abu-Absi et al.; "Real-time monitoring of multiple parameters in mammalian cell culture bioreactors using an in-line Raman spectroscopy probe"; Biotechnol. Bioeng. 108 (5) (2001) 1215-1221 (Year: 2001).*
Feng Li et al.; "Cell culture processes for monoclonal antibody production"; mAbs 2:5, 466-477; 2010 Landes Bioscience (Year: 2010).*
Matthew S. Croughan et al.; "The Future of Industrial Bioprocessing: Batch or Continuous?"; Biotechnology and Bioengineering, vol. 112, No. 4, Apr. 2015 (Year: 2015).*
Ravendra Singh et al. "An ontological knowledge-based system for the selection of process monitoring and analysis tools"; Computers and Chemical Engineering 34 (2010) 1137-1154 (Year: 2010).*
Chunguang Liang et al; "GoSynthetic database tool to analyse natural and engineered molecular processes"; Database, vol. 2013, Article ID bat043, doi: 10.1093/database/bat043 (Year: 2013).*
Andrew Campbell et al.; "Concise Review: Process Development Considerations for Cell Therapy"; Stem Cells Translational Medicine 2015;4:1155-1163 (Year: 2015).*
Timo Schmidberger et al.; "Progress Toward Forecasting Product Quality and Quantity of Mammalian Cell Culture Processes by Performance-Based Modeling"; Biotechnol. Prog., 2015, vol. 31, No. 4 (Year: 2015).*
M. Sandor et al.; "Comparative study of non-invasive monitoring via infrared spectroscopy for mammalian cell cultivations"; Journal of Biotechnology 168 (2013) 636-645 (Year: 2013).*
Alexandros-Dimitrios Kyparissidis; "Development of a combined mathematical and experimental framework for the control and optimisation of mammalian cell culture systems;" A thesis submitted for the degree of Doctor of Philosophy; (Year: 2012).*
Bassem Ben Yahia et al; "Macroscopic modeling of mammalian cell growth and metabolism"; Appl Microbiol Biotechnol (2015) 99: 7009-7024 (Year: 2015).*
R. Lencastre Fernandes et al; "Experimental methods and modeling techniques for description of cell population heterogeneity"; Biotechnology Advances 29 (2011) 575-599 (Year: 2011).*
Chetan T. Goudar; "Computer programs for modeling mammalian cell batch and fed-batch cultures using logistic equations"; Cytotechnology (2012) 64:465-475 (Year: 2012).*
Mathias Aehle et al; "Increasing batch-to-batch reproducibility of CHO-cell cultures using a model predictive control approach"; Cytotechnology (2012) 64:623-634 (Year: 2012).*
European Search Report for EP Application No. 18817323.1 mailed Jun. 28, 2021 (10 pages).
Craven et al., "Glucose Concentration Control of a Fed-Batch Mammalian Cell Bioprocess Using a Nonlinear Model Predictive Controllers," Journal of Process Control, 2014, 24:344-357.
Van Breusegem et al., "Adaptive Neural Models for On-line Prediction in Fermentation," The Canadian Journal of Chemical Engineering, 1991, 69:481-487.
PCT International Search Report and Written Opinion for PCT Application No. PCT/IN2018/050398 mailed Sep. 19, 2018 (8 pages).
Japanese Office Action for corresponding JP Patent Application No. 2019-569403, mailed Feb. 28, 2022 with Summary of JP Office Action in English (8 pages).
Journal of Process Control, 2014, vol. 24, p. 344-357.
Hughes, T.A. "Measurement and Control Basics", 1995, 2, pp. 11-17.
Japanese Office Action for JP Application No. 2019-569403 mailed Sep. 5, 2022 (13 pages, with English Translation).
Chinese Office dated Mar. 4, 2023, 20 pages and Search Report, dated Mar. 2, 2023, 3 pages, for CN Application 201880052944.X.
Luo Rongfu, et al., "Modelling and Simulation of CHO Cells Growth Process", Chinese Journal of Biotechnology, Oct. 23, 1994, pp. 356-361.

(56) References Cited

OTHER PUBLICATIONS

Ricardo Aguilar-Lo'pez, et al., "Exponential Observer Design for State Estimation in a Class of Anaerobic Sulfate Reducing Bioreactor", Chemical Product and Process Modeling, Dec. 31, 2009, pp. 1-12.

* cited by examiner

METHOD FOR PREDICTING OUTCOME OF AN MODELLING OF A PROCESS IN A BIOREACTOR

CROSS REFERENCE TO RELATED APPLICATIONS

This application claims the priority benefit of PCT/IN2018/050398 filed on Jun. 18, 2018, which claims priority benefit of Indian patent application Ser. No. 20/174,1021125 filed on Jun. 16, 2017, the entire contents of which are hereby incorporated by reference herein.

TECHNICAL FIELD

The present invention relates to the field of predicting outcome of and modelling of a process in a bioreactor, especially a method for predicting outcome of and modelling of a process used for manufacturing a sample intended to be used in another system.

BACKGROUND

Users of single-use bioreactors routinely engage in process development and process optimization as part of their research and manufacturing activities, which requires months of work to get the best result. Additionally, during runs, anomalies in the cell culture process (Cell Therapy or Bio-Process) is not detected by instrumentation and, in absence of an automated remote monitoring and diagnostic environment, human supervision is the only check to save a batch.

A digital twin may be used to modelling a process, e.g. a bioreactor, to predict the outcome from a process run ahead of time, provided the digital twin has access to a process model that accurately describe the process run. Users spend huge effort on developing protocols for the process runs to ensure maximal growth of cells, and continue to invest in optimizing the process. This is currently through trial and error, vanilla statistical techniques, and experience.

Thus, there is a need to develop a procedure for creating process models that can serve as a digital representation of a process used for manufacturing a sample in a biological system, such as a bioreactor.

Cell growth is a highly non-linear process, following 4 phases of growth—linear, exponential, stationary and death phase. It is also highly variable, and can be influenced in complex fashion by several known and unknown environmental and genetic factors, with the result that two successive cell culture batches can follow very different growth patterns.

In this context, being able to predict features such as viable cell concentration, total cell concentration, product or metabolites accurately a few days in advance for every cell culture set up; and also identifying patterns in cell growth can lead to improved logistics, and optimized pharmaceutical workflows.

Currently, the approaches used for solving similar problems include using standardized tools like SIMCA. These are broad purpose tools, but they have a few drawbacks:
1) Tools like SIMCA use standard statistical approaches, but
   a. Are not customized for solving specific problems
   b. Do not have a self-learning framework.
2) Additionally, these tools typically need multiple parameters Evaluation of data from bioprocesses is normally performed off-line and post-run. In addition, the evaluation is not done as a comparison to the "expected outcome". One reason is the lack of connectivity for different sources of data, e.g. log data, in-process-controls, product quality data, etc. Another reason is the inability to adequately model the performance of the bioprocess.

SUMMARY

An object of the present disclosure is to provide methods and devices configured to execute methods and computer programs which seek to mitigate, alleviate, or eliminate one or more of the above-identified deficiencies in the art and disadvantages singly or in any combination.

The object is achieved by a method for predicting outcome of a process used for manufacturing a sample in a bioreactor, the process belonging to a category. The method comprises selecting a process model based on the category; accessing historic data related to past process runs for manufacturing the sample; and accessing current data obtained from a current process run of the process. The obtained current data, which is based on the selected process model, comprises: process strategy data, bioreactor instrument data, data from online sensors and/or data from offline sensors. The method further comprises predicting an outcome of at least one selected parameter of the current process run for manufacturing the sample based on the accessed historic data and current data.

An advantage is that an undesired behaviour of a selected parameter may detected ahead of time and measures may be instituted that will affect the outcome.

The object is also achieved by a method for modelling of a process used for manufacturing a sample in a bioreactor, the process belonging to a category. The method comprises selecting a process model based on the category; accessing historic data related to past process runs for manufacturing the sample; and accessing current data obtained from a current process run of the process. The current data, which is based on the selected process model, comprises: process strategy data, bioreactor instrument data, data from online sensors and/or data from offline sensors. The method further comprises predicting outcome at least one parameter of the current process run for manufacturing the sample; and updating the process model based on historic data and the monitored at least one parameter when the current process run is completed.

An advantage is that a process model used to model a process is automatically updated based on the results from the previous process run.

The object is also achieved by a control system for controlling a process used for manufacturing a sample in a bioreactor, the process belonging to a category. The control system is configured to simulate the process and is further configured to select a process model based on the category; access historic data related to past process runs for manufacturing the sample; and access current data obtained from a current process run of the process. The obtained data, which is based on the selected process model, comprises: process strategy data, bioreactor instrument data, data from online sensors and/or data from offline sensors. The control unit is further configured to predict an outcome of at least one selected parameter of the current process run for manufacturing the sample; and to control the process used for manufacturing the sample in a bioreactor based on the predicted outcome of the at least one selected parameter of the current process run.

Further objects and advantages may be obtained from the detailed description by a skilled person in the art.

DETAILED DESCRIPTION

Figure 1:
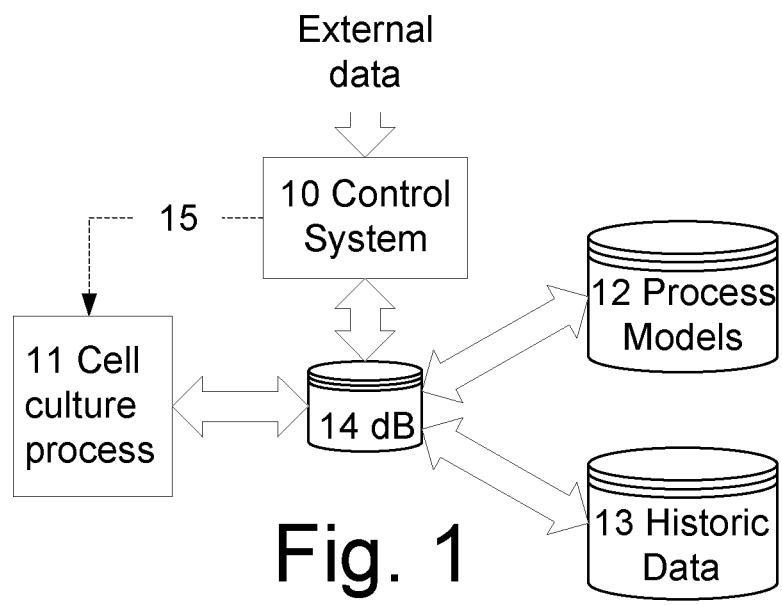
FIG. 1 illustrates a control arrangement for modelling of a process used for manufacturing a sample in a bioreactor.

The term "process model" refers to the proprietary model of the cell culture process which can forecast outcomes of interest and enables "what if" analysis for process optimization.

The term "feed" refers to the solution that is added to the culture to prevent nutrient depletion.

The term "media" refers to the base liquid or gel designed to support the growth of cells. A typical media comprises of amino acids, vitamins, inorganic salts, glucose, serum etc.

The term "cell-line" refers to a cell culture developed from a single cell and therefore consisting of cells with a uniform genetic make-up.

The term "clone" refers to an organism or cell, or group of organisms or cells, produced asexually from one ancestor or stock, to which they are genetically identical.

The term "outcome" refers to the measurable output/product of a cell culture. This can be cells, proteins, by-products like lactate, ammonium etc.

The term "strategy" refers to the protocol for process parameters like feed regime, instrument set points (e.g. pH, DO, CO2) etc.

The term "supplement" refers to additional nutrients added apart from feed and base media.

The term "capture" means in the context of a chromatography method the first chromatography step, wherein a large amount of target compound is captured or, for a flow-through process, a large amount of impurities is captured.

Digital representation of a process used for manufacturing a sample in a biological system, such as a bioreactor, is desired in order to be able to evaluate and improve the process before it is used to manufacture the sample. A ramification of this premise is that the associated process model, used as a digital representation, may require self-learning capabilities and novel analytics to faithfully represent the biological system.

The advantage with a digital representation is that a result of the process may be predicted, such as an outcome (e.g. cell viability, cell count, product titre, product quality, etc.). There is no direct causality between instrument parameters (e.g. pH, rocking rate, rocking angle, temperature, oxygen/$CO_2$ control, etc.), user control factors (e.g. feed, feed strategy, media, clone, glucose Stock Solution, etc.), and these outcomes.

In order to obtain good prediction from a digital representation (i.e. a process model), outcomes has to be modelled as a function of instrument parameters and measured parameters using offline/online sensors of the biological system, e.g. the cell culture process, during a current process run. Examples of measured parameters are: pH, dissolved $O_2$, $CO_2$, Glucose, Glutamine, Glutamate, Lactate, Ammonium, Sodium Ion, Potassium Ion, Osmolality, etc.

Recommended instrument parameters depend on the reactor type used (e.g. shake flask or stir tank) and comprises: pH, rocking rate, rocking angle, stirring rate, impeller speed, temperature, oxygen/$CO_2$ control, aeration rate, etc. Studies regarding which instrument parameters influence cell growth have been performed, but so far there is no comprehensive model to find optimal values for the instrument parameters and other related parameters, such as calculated amount of supplement provided, feed rates, feed strategies, etc. In the prior art, optimal settings are typically obtained after significant process development and process optimization efforts. However, if an analytic approach is implemented involving domain knowledge, process data and historic data, i.e. incorporating domain knowledge into statistical understanding of the process data, the efforts required to arrive at optimal instrument parameters and perform "what-if" analysis will be significantly reduced.

Thus, the disclosed process models are analytic in nature as they self-learn from past process runs, or historic process runs, to predict outcomes from the current process run. The model can also incorporate information from soft sensors, in line sensors, and commercial asset performance management solutions to refine predictions of outcomes. These analytic models automatically fine tune predictions of the current process for manufacturing a sample, e.g. using Kalman Filters.

Furthermore, in prior art systems anomalies, e.g. contaminants, metabolites out of boundary values, are detected only through human supervision. The disclosed process models are able to detect patterns from offline measurements made and thereby detect anomalies early. This information may be used by the operator to take necessary corrective action or actions to improve yield from the process run.

FIG. 1 illustrates a control arrangement for adaptive modelling of a process used for manufacturing a sample in a biological process, such as a bioreactor used in a cell culture process 11. The control arrangement comprises a control system 10 which is configured to model the cell culture process and is further configured to: select a process model, access historic data, access current data from a current process run and predict an outcome of at least one selected parameter of the current process run for manufacturing the sample.

The process model is selected based on the type of process used to manufacture a sample in the cell culture process 11. A system to categorize the different processes is disclosed in connection with FIG. 3, in which each process is assigned to a category and is stored in a database for process models 12. Historic data related to past process runs for manufacturing the sample is accessed from a database with historic data 13, and current data is accessed from a current process run of the process, as described in connection with FIG. 2. Historic data comprises data of completed process runs or experiments and the typical data is similar to the data obtained from a current process run.

As mentioned above, the control unit is also configured to predict an outcome of at least one selected parameter. This includes cell viability, cell counts, product titre, product quality, etc.

According to some aspects, a database 14 is used for consolidating historic data, current data and data related to the process model. All data related to the current and past processes, in addition to the data related to the process model are consolidated and stored in a place for easy access.

The control unit 10 may also be configured to control the process used for manufacturing the sample in a bioreactor based on the predicted outcome of the at least one selected parameter of the current process run, as indicated by the dashed arrow 15.

Figure 2:
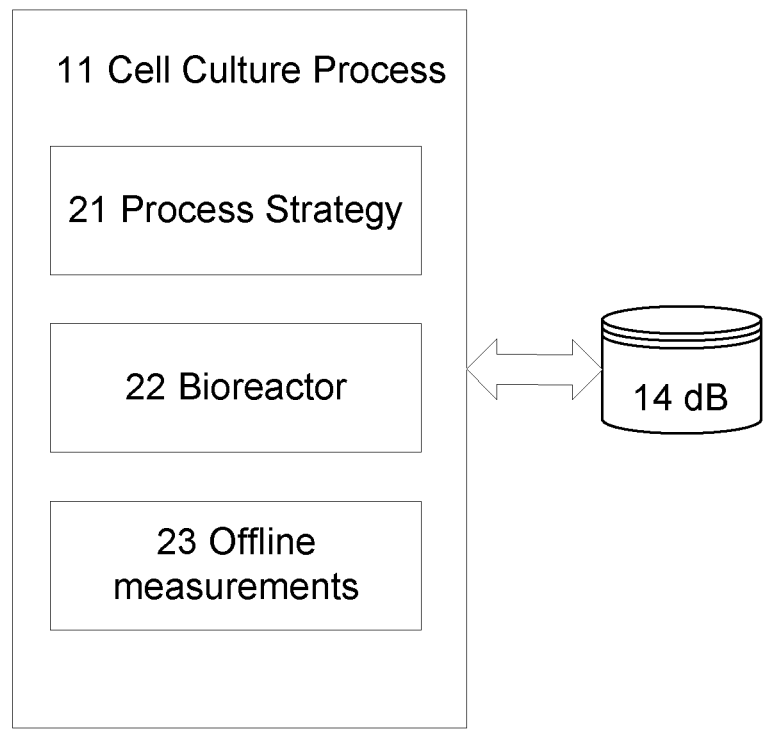
FIG. 2 illustrates extracting current data from a current process run into a database.

FIG. 2 illustrates extracting current data from a current process run into a database 14. The current data is obtained from the Cell culture process 11 and is based on the selected process model from the process model database 12 and the current data comprises: process strategy data 21, bioreactor data 22 (including instrument data and data from online sensors), and/or data from offline measurements 23.

Process strategy data 21 comprises strategy information regarding the process as such, e.g. media, feed type, feed regime, supplements (type and concentration) & supplements regime, etc. Bioreactor data 22 comprises data related to the process from the Bioreactor instrument (e.g. agitation, aeration, etc.) and any available online sensors attached to the Bioreactor (e.g. pH, dissolved $O_2$, etc.). Offline measurement data 23 comprises data related to process samples measured on offline sensors (e.g. data for cell count, product titre, metabolites concentration, partial pressure of gasses, etc.).

When extracting data from the cell culture process 11, this is performed based on the selected process model in order to optimize resources needed to obtain the required data.

Figure 3:
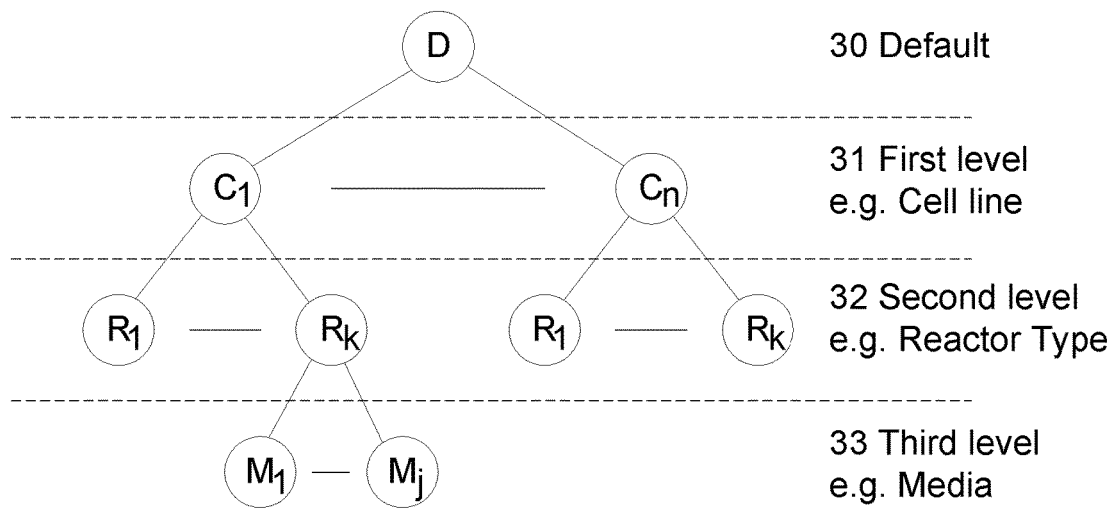
FIG. 3 shows an example of how different processes are categorized in order to assign a suitable process model to a process.

FIG. 3 shows an example of how different processes are categorized in order to assign a suitable process model to a process. The system comprises a number of levels representing the detail of categorization made, such as a default level 30, first level 31, second level 32, third level 33, etc. This information is stored in a database for process models 12. It should be noted that the description below is only an example of how the categorization may be applied, and other features for category selection may be used, e.g. scale-up/scale-down.

In the example, the default level 30, a default process model "D" is a basic process model used and assigned to any process that has not been previously categorized. The first level 31 represents in this example process models for based on cell lines, $C_1, \ldots, C_n$, wherein different cell lines may require an adapted process model in order to predict an outcome correctly. Each process model may in turn be further adapted based on e.g. reactor type $R_1, \ldots, R_k$, as illustrated in the second level 32. In this example some of the process models for cell line $C_1$ and reactor type $R_k$ has further been adapted based on media, $M_1, \ldots, M_j$, as illustrated in the third level 33.

Depending on the process, a corresponding process model is selected by the control system 10 and used for a current process run. The process to categorize a process into a suitable process model is described in more detail in connection with FIGS. 5 and 6.

Figure 4:
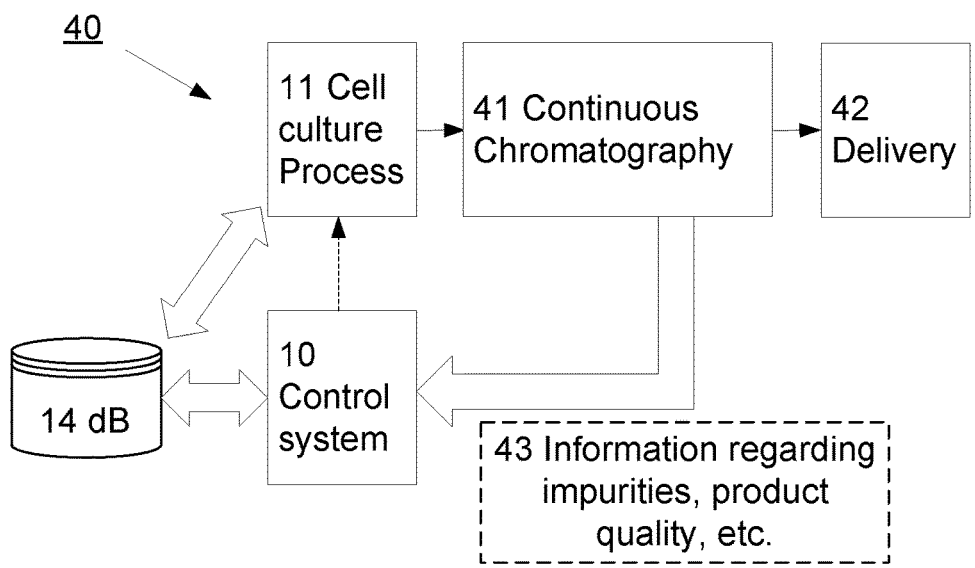
FIG. 4 illustrates a system for producing a product based on a sample created in a cell culture process.

FIG. 4 illustrates an example embodiment of a system 40 for producing a product based on a sample created in a cell culture process 11. The control system has been described in connection with FIG. 1 and has access to a consolidated database 14 containing all data related to the current and historic process runs.

In view of chromatography systems, the term "sample" refers to a liquid which contains two or more compounds to be separated. In this context, the term "compound", or "product", is used in a broad sense for any entity such as a molecule, chemical compound, cell etc. The term "target compound", or "target product" means herein any compound which it is desired to separate from a liquid comprising one or more additional compounds. Thus, a "target compound" me be a compound desired e.g. as a drug, diagnostic or vaccine; or, alternatively, a contaminating or undesired compound which should be removed from one or more desired compounds.

The system 40 further comprises a capture step, in this example illustrated by a continuous chromatography system 41, into which the sample from the cell culture process 11 is fed. The sample comprising a target product. The continuous chromatography system 41 capture the target product to be delivered 42. The continuous chromatography system 41 measures a number of parameters in order to obtain an efficient high quality manufacturing process and information 43 regarding impurities, product quality, etc. may be transferred to the control system 10. This information may be used to further adapt the process model and to control the cell culture process 11 in order to increase the performance of the complete system and provide an improved yield.

Figure 5:
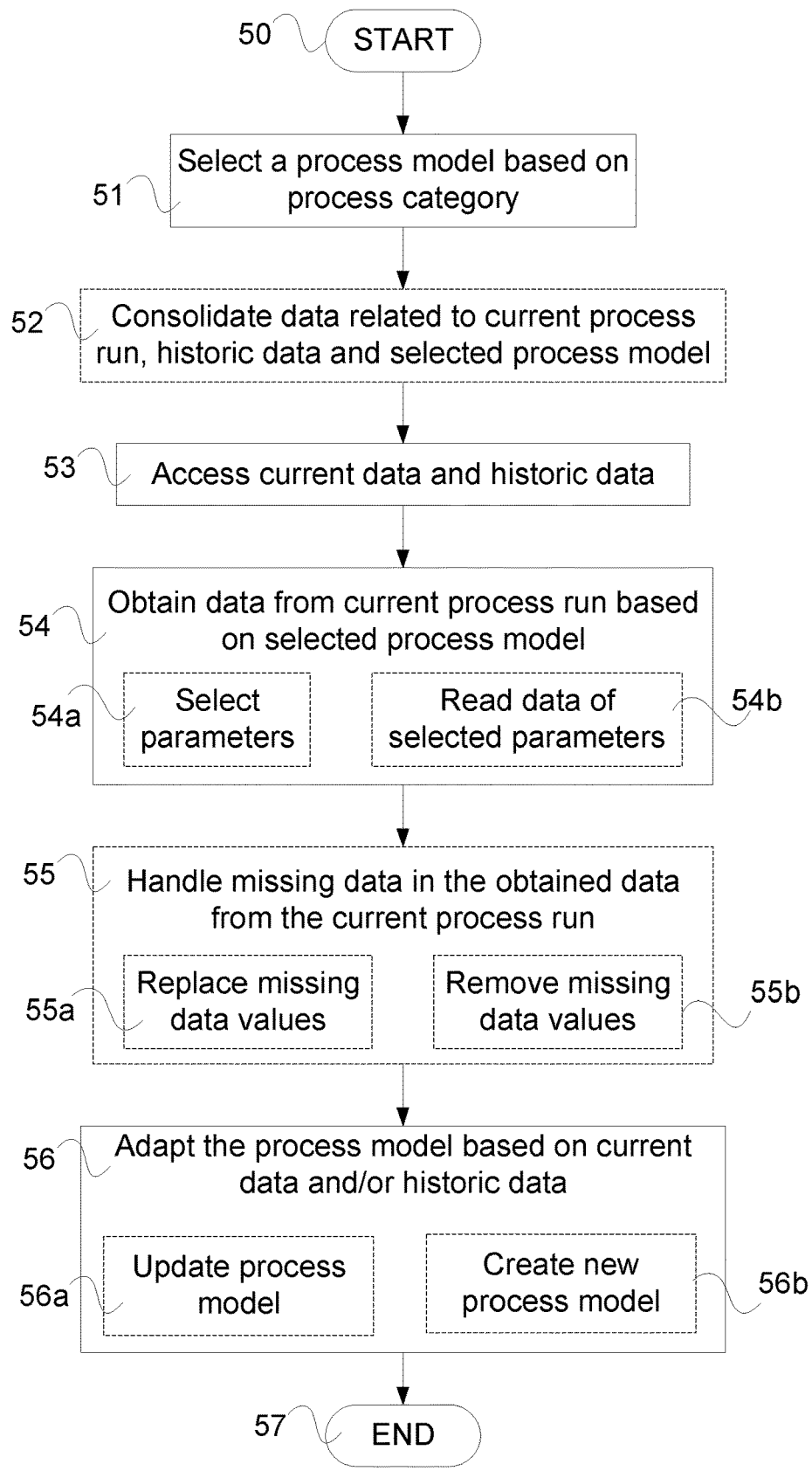
FIG. 5 illustrates a flowchart for adaptive modelling of a process used for manufacturing a sample in a bioreactor.

FIG. 5 illustrates a flowchart for adaptive modelling of a process used for manufacturing a sample in a bioreactor, the process belonging to a category. Each process used to manufacture a sample is assigned to a default category, unless a category has been assigned to the current process.

The process starts at 50 and in step 51, a process model is selected based on the category, as described in connection with FIG. 3. The selected process model defines relevant data to be obtained from the cell culture process 11.

Step 52 is an optional step, which comprises consolidating historic data, current data and data related to the process model in a database, as described in connection with FIG. 1.

In step 53 historic data is accessed either from a separate database or in a consolidated database. The historic data is related to past process runs for manufacturing the sample and comprises data of completed process runs or experiments.

In step 53, current data is accessed either directly from the cell culture process or from a consolidated database. The current data comprises: process strategy data, bioreactor instrument data, data from online sensors and/or data from offline sensors, as described in connection with FIG. 2.

The accessed data is based on the selected process model, and in step 54 the current data is obtained from a current process run of the process in the cell culture process. This step enables accommodation of additional or less process data of the parameters in comparison to data required by the process model.

According to some aspects the input parameters are selected, step 54a. Either automatically based on available data and the process model, or user specified input parameters is used, wherein a user of the system selects parameters in addition to the mandatory parameters required by the process model.

According to some aspects, data of selected parameters is read to be available for further processing in step 54b.

Step 55 is an optional step in which missing data in the current data obtained from the current process run is handled and enables the process model to perform data imputation when encountered with missing data.

According to some aspects, a missing data value is replaced with an imputed value based on historical trends, interpolation and predictions based on other available data of the parameters in step 55*a*.

According to some aspects, data with missing data values are removed, i.e. clean data with missing values, in step 55*b*. Data is preferably removed only when determined not to materially affect the predictions.

In step 56, at least one parameter of the current process run for manufacturing the sample is monitored and the process model is adapted in real-time based on historic data and/or the monitored at least one parameter when the current process run is completed. This step provides the process model a capability to adapt the process model for different cell lines, clones, reactor types, media, etc. This reduces the need to manually build process models for each variation. Self-learning helps to adjust the prediction errors of the process model for improved accuracy.

The purpose of this step is to train and update the process models, either by updating a process model or create a new process model, based data from completed process runs or experiments. Techniques used for self-learning is Kalman Filters, Fuzzy logic etc.

According to some aspects, the step of adapting the process model further comprises updating the process model for the category, step 56*a*, using historic data for better predictions or forecasts.

According to some aspects, the process used in the current process run is determined to belong to a new category and the step of adapting the process model further comprises creating a new process model (step 56*b*) by: assigning the process to the new category; and storing the process model as a new process model.

The process ends in step 57.

The process described in connection with FIG. 5 may be implemented in a computer program for modelling of a process used for manufacturing a sample in a bioreactor. The computer program comprises instructions which, when executed on at least one processor, cause the at least one processor to carry out the method described in FIG. 5. The computer program may be stored on a computer-readable storage medium.

Figure 6:
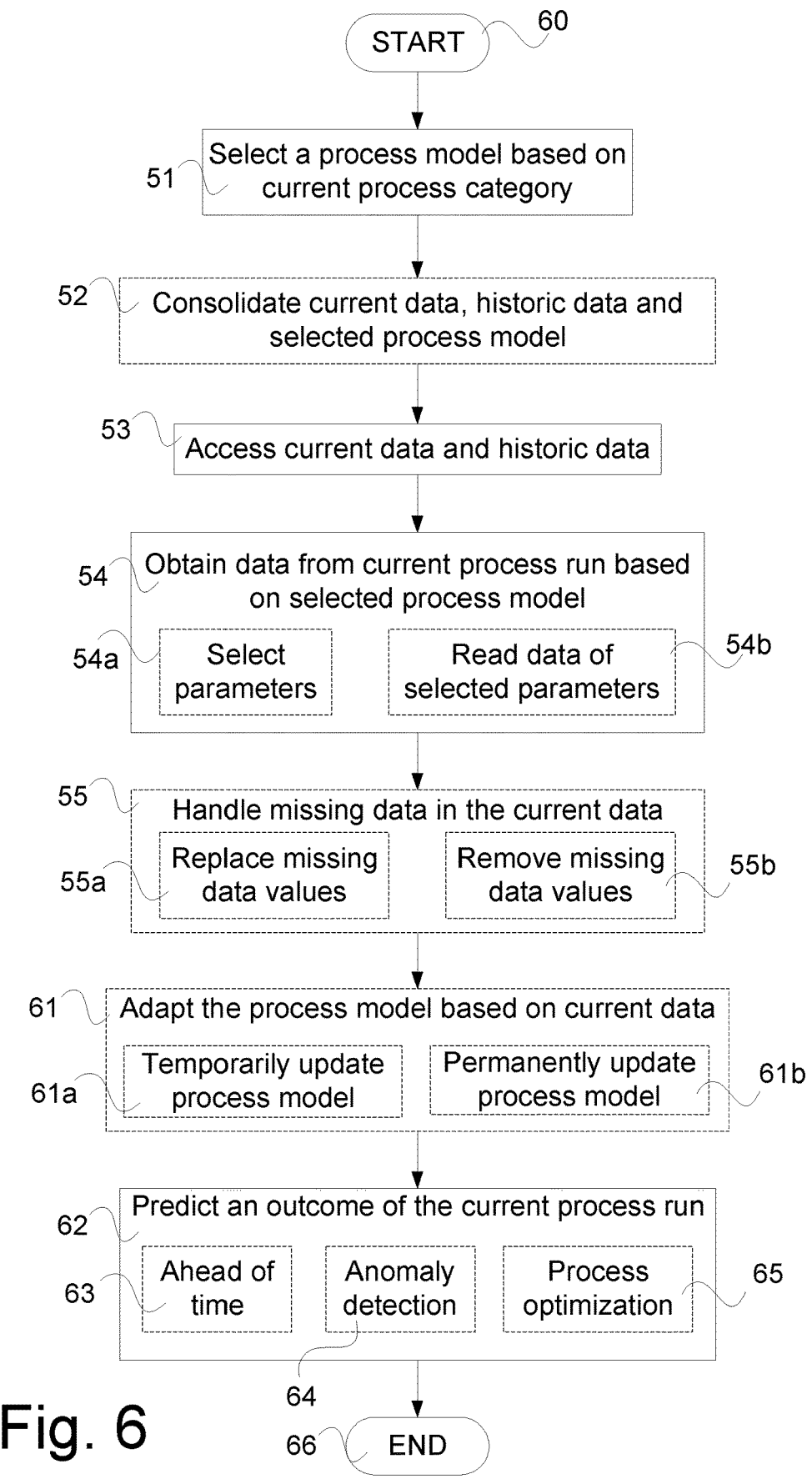
FIG. 6 illustrates a flowchart for predicting outcome of a process used for manufacturing a sample in a bioreactor.

FIG. 6 illustrates a flowchart for predicting outcome of a process used for manufacturing a sample in a bioreactor, the process belonging to a category. Each process used to manufacture a sample is assigned to a default category, unless a category has been assigned to the current process.

The process starts at 60 and continuous to steps 51, 52, 53, 54 and 55, which have been described in connection with FIG. 5. These steps include:

Step 51—selecting a process model based on the category.

Optional step 52—consolidating historic data, current data and data related to the process model in a database.

Step 53—accessing historic data related to past process runs for manufacturing the sample in step and accessing current data obtained from a current process run of the process.

Step 54—obtaining current data based on the selected process model. The current data comprises: process strategy data, bioreactor instrument data, data from online sensors and/or data from offline sensors. According to some aspects the input parameters are selected, step 54*a*. Either automatically based on available data and the process model, or user specified input parameters is used. According to some aspects, data of selected parameters is read to be available for further processing in step 54*b*.

Optional step 55—handling missing data in the current data obtained from the current process run and enabling the process model to perform data imputation when encountered with missing data. According to some aspects, a missing data value is replaced with an imputed value based on historical trends, interpolation and predictions based on other available data of the parameters in step 55*a*. According to some aspects, data with missing data values are removed, i.e. clean data with missing values, in step 55*b*.

In optional step 61, at least one parameter of the current process run for manufacturing the sample is monitored and the process model is adapted based on the monitored at least one parameter during the current process run. This step provides the process model a capability to adapt the process model for different cell lines, clones, reactor types, media, etc. This reduces the need to manually build process models for each variation. Self-learning helps to adjust the prediction errors of the process model for improved accuracy.

The purpose of this step is to train and update the process models, either by temporarily or permanently, based on obtained data from process runs or experiments. Techniques used for self-learning is Kalman Filters, Fuzzy logic etc.

According to some aspects, the step of adapting the process model further comprises updating the process model for the category, step 61*a*, using new data from the current process run and temporarily updating the process model as "new" process model for the category, i.e. applying the updated process model when predicting the outcome from the current process run. At the end of the process run, the original process model is restored for the category.

According to some aspects, the "new" process model is permanently stored for the category in step 61*b*, i.e. the updated process model is applied when predicting the outcome in future process runs using a process belonging to this category.

According to some aspects, the process used in the current process run is determined to belong to a new category and the step of adapting the process run further comprises assigning the process to the new category; and storing the process model as a new process model.

In addition to refining the process models, the actual predictions during the process run may also be updated based on measured values vs. predicted values.

The process continuous with the final step 62, in which an outcome of at least one selected parameter of the current process run for manufacturing the sample is predicted based on the accessed historic data and current data.

According to some aspects, the step of predicting the outcome of at least one selected parameter further comprises at least one of the following:

predicting a forecast of the at least one parameter, step 63. The outcomes of interest are predicted ahead of time, until the end of the current process run.

predicting a forecast of anomalies, step 64. Anomalies are predicted ahead of time, e.g. metabolite concentration out of expected ranges in 24 hours if no adjustments is made to the cell culture process.

determining and recommending actions to obtain improved conditions for the current process run, step 65. Prescribes the conditions that can optimize the process.

The process described in connection with FIG. 6 may be implemented in a computer program for predicting outcome a current process run for manufacturing a sample in a bioreactor. The computer program comprises instructions which, when executed on at least one processor, cause the at least one processor to carry out the method described in FIG. 6.

The computer program may be stored on a computer-readable storage medium.

As mentioned above, current solutions to predict cell growth in a bioreactor has a few drawbacks. In contrast, our approach learns with time to create the best possible forecasts.

Furthermore, the disclosed process is a lean approach. It can work with a minimal set of parameters, but can use more parameters if available.

In summary, a method, and a system, is provided which has a self-evolving data based approach to learning patterns of cell growth. This can be used for
- a) Prediction of various outcome parameters/metabolites of the current process runs such as viable cell concentration and product concentration
- b) Identifying anomalous growth patterns and
- c) Learn relationships between cell growth outcome parameters and various levers of experimental control.

A system is disclosed for predicting features such as viable cell concentration, total cell concentration, product or metabolites days in advance. This is a step wise approach, where coarser predictions are made in the earlier steps, and refined at later steps.

It is required that the system has access to a database containing historical data of output and input features from past process runs stored in the database, e.g. indexed by experiment ID, either in raw format or potentially as a knowledge tree based on some distance/nearness criteria such as Euclidean distance, etc.

After the current process run is complete, it is added to this database as well (at the appropriate location if it is a tree).

Figure 7:
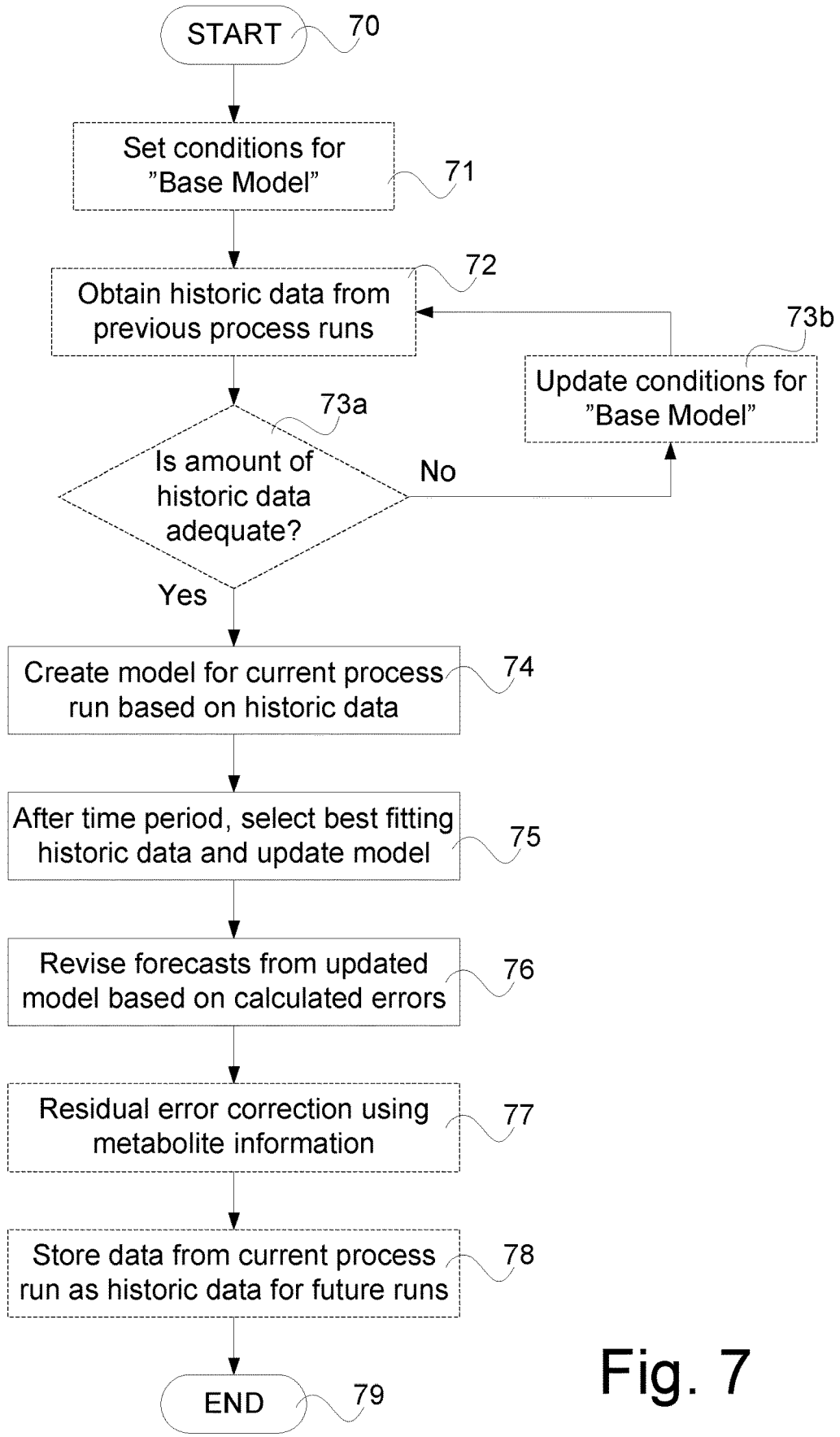
FIG. 7 illustrates a flowchart for predicting features in advance when manufacturing a sample in a bioreactor.

FIG. 7 illustrates a flowchart for an alternative process for predicting features in advance when manufacturing a sample in a bioreactor. The process is a curve evolution approach, which is based on a series of steps to improve the possibility to predict the outcome, or forecasts for a feature, of a process for manufacturing a sample in a bioreactor during a process run.

Figure 8A:
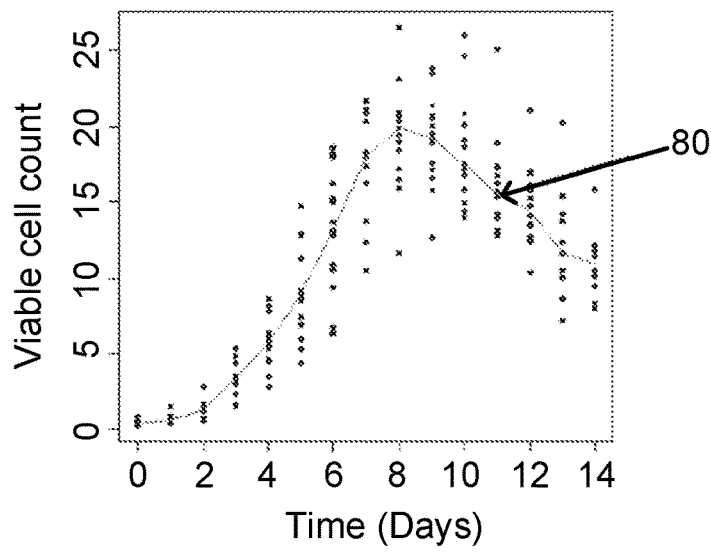
FIGS. 8a-8c illustrate different steps in a process to predict features in advance using the process described in connection with FIG. 7.
Figure 8B:
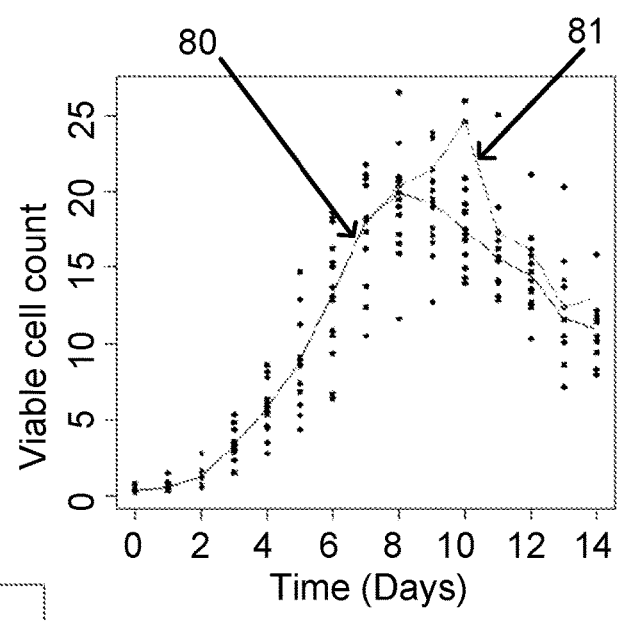
Figure 8C:
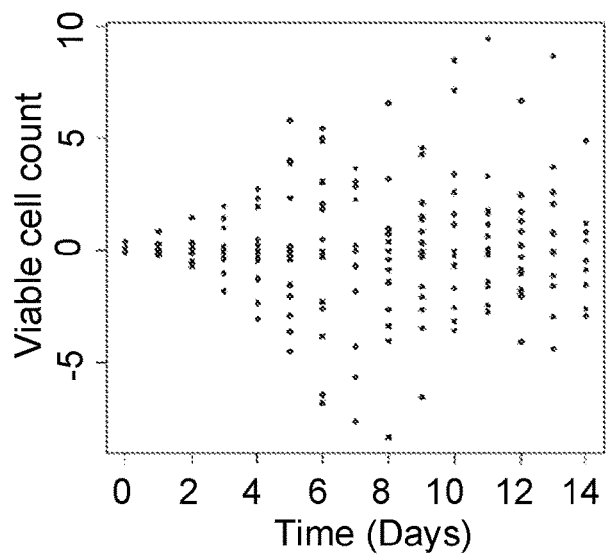

The process is illustrated together with FIGS. 8a-8c, and has 4 steps, in a step wise approach, coarser predictions are made in earlier steps, and refined at later steps:

step 1) Fitting an overall base model to historic data—illustrated in FIG. 8a. This is a base model which takes a simple mean/median/polynomial fit of the historic data in the database versus culture time. According to some embodiments, all the process runs in the database are used. According to some embodiments, a subset of only those process runs which satisfy certain conditions, i.e. pre-existing knowledge (e.g. choose only experiment in database which use same media as current process run) to give a more relevant estimate.

step 2) Improving base model in real time based on curve evolution—illustrated in FIG. 8b. At every time period T from the start of process run as the current process run is progressing, this step comprises running a pattern match of the current process run's time series until the current time, against all process runs in the database till time T, to identify the closest K matches which satisfy a certain distance threshold. We can now update all predictions from T till the end of the batch by repeating the step 1 methodology, but only on the K closest matches. This ensures that we correct the forecasts issued by step 1 to a more accurate number by learning from other historical process runs. This step is repeated at every T.

step 3) Building model from fed back errors—Illustrated in FIG. 8c. At time T, the prediction made for time T+ forecast horizon after applying step 2 is further refined by building a model on historical process runs in the database f (or a subset as chosen from step 2), to predict how errors made in all the forecasts till the current time of experiment are able to predict errors made in the future, and update current prediction made after step 2 by this error.

step 4) Adding covariate information to correct predictions further (optional step). Explicitly using measured metabolites like glucose, lactate, etc. to build a model of errors g after applying step 3 against metabolite information, to further refine forecasts.

Prediction of how cell growth/product production by cell is going to evolve a few days in advance is a hard problem, as cells are complex and affected by several factors. An associated challenge is identifying anomalous growth patterns in advance, and identifying if recovery from anomalous growth is possible by changing the cell environment operationally, and if so, how.

The system described herein is a continually learning prediction system, which learns from other historical process runs in the past, and also from previous data points of the current experiment in a feedback mode, to issue accurate predictions.

The learning from other process runs step (Model 2) can be used for other associated functions as well, such as identifying bad or unrecoverable process runs, and emerging anomalies by comparing to other flagged anomalous process runs in the past, or deviations from normal process runs.

In addition, this system can also be used to predict interesting experimental outcomes, such as the time when cell growth peaks, the time when cell viability reaches a certain threshold, etc. which can be of use to the experimentalist for logistical purposes.

The system described herein can also be potentially extended to understand how cell growth is influenced by measured parameters, and in experimental design, by looking at multidimensional cluster patterns.

Step 71 is an optional step in which conditions for the Base Model, BM, for the process run is set. If this step is omitted, the base model is created based on the historic data from all previous process runs. In optional step 72, historic data matching the conditions set in step 71 is obtained from previous runs (which normally are stored in a database accessible to the system.

As explained below, in order to make a base model, historic data needs to be provided and if the conditions, for instance, are too tight, there might be difficult to find relevant process runs in the historic data. This is controlled in optional step 73a. If not, the process continues to step 73b, where the conditions for the base model is updated before new historic data is obtained in step 72.

On the other hand, if adequate amount of historic data is obtained, the process continues to step 74 to create a model, in this disclosure called "Base Model", based on historic data. The historic data may be selected based on conditions set in step 71.

In brief, step 74 builds a coarse model based on mean/median/any curve fit, indicated by 80 in FIG. 8a, of all the data which is similar to the current experiment for which prediction has to be made. Similarity can be similar conditions (similar reactor, media, cell line), or a more sophisticated measure of similarity.

For example, when starting on day "0", a prediction for the course of the batch for a specific cell line (e.g. a CHO cell line), grown in an 5 litre stirred bioreactor, in a particular media, is made. All previous process runs in the historical database which have a similar cell line, and have been grown in a similar bioreactor, with similar media are considered and are selected. This subselected set of historic process runs is called E1. The mean/median/polynomial fit of all these process runs E1 is calculated, and is indicated with reference numeral 80 in FIGS. 8a and 8b, to get an estimate of prediction for the current process run.

Note that this "similarity" can be defined any way, it may be a more looser similarity threshold if no sets of previous process runs from the historic data match the conditions of the current process run, or have a tighter threshold if there are exactly run batches with the same conditions in the past.

This similarity threshold can also depend on the stage of the pharma workflow, a tighter similarity threshold might be desire in manufacturing, and a looser threshold in process development.

In step 75, as the current process run progresses through time, the set of similar process runs used to build the model keep changing. This helps in continuously refining predictions.

Continuing the example above, while a set of process runs E1 which are similar are selected to build the base model, in step 75, amongst the process runs in E1, all previous process runs which are closest to the time series of the current process run up to that particular day are chosen, this model is called Base Model with Learning, BMWL.

For example, when on day "5", there is 5 days of the current process run. If a prediction for day 6-day 10 is desired, the subset of E1 whose time series from day 0 to day 5 (in a univariate or multivariate sense) is closest to the current process run is considered. Let this subset be E2, and then calculate mean/median/any curve fit, as indicated by reference numeral 81 in FIG. 8b, using only process runs in E2 to issue predictions for the current process run from day 6 to day 10. This will give finer predictions than the base model in step 74, as the set of process runs used to build the model are revised.

Note that this list of process runs may change with time, as the current process run evolves In step 76, the forecasts issued by step 75 is revised to create finer forecasts. The errors made by the forecasts, as explained above, are fed back to improve future forecasts at the next time instant. In other words, we build a model of form $$\varepsilon_{T+LookAh} = f(\varepsilon_{T, T-1..0})$$

Where $\varepsilon_T$=Actual Val$_T$−BMWL Forecast$_T$ represents error between actual data and forecasts from the Base Model with Learning, BMWL, at time T during the historic process run.

This error is used to update current prediction made using the BMWL as follows $$BMWL(+EC)Forecast_{T+LookAhead} = BMWL\ Forecast_{T+LookAhead} + \varepsilon_{T+LookAhead}$$

BMWL(+EC) stands for Base Model with Learning and Error Correction.

In step 77, which is an optional step, Residual error correction using metabolite information is applied. This step revises forecasts from step 76, by regressing remaining error between step 76 forecasts and actual data against measured metabolite information such as glucose, lactate, ammonia, etc. The metabolite information is preferably measured in advance and stored in a database accessible to the system.

In other words:

$$\text{Model "step77"} Forecast_{T+LookAhead} = BMWL(+EC)\ Forecast_{T+LookAhead} + \alpha_{T+LookAhead}$$

where $\alpha_{T+LookAhead}$=g(Metabolite information$_{T, T-1..0}$) $\alpha_T$=Actual Val$_T$−BMW L(+EC) Forecast$_T$ In step 78 the data from the current process run is stored as historic data for future process runs. The historic data is normally stored in a database accessible to the system.

The technical advantage with method described above is that it allows for a system which continuously learns from new data, to ensure it can predict output features as accurately as possible. Since this is entirely automated, it also obviates the need to manually build, and update, custom solutions/models for each type of bioreactor or each experimental setup. As it is continuously fed more data, it also keeps getting more powerful with time as its learning repository gets bigger.

The commercial advantages are that doing so enables
 a) Time and cost savings in process development and manufacturing workflows in the pharmaceutical industry,
 b) Faster detection of emerging anomalies, which can help save the batch by adding required metabolites, or taking a decision on faster abortion of the experiment, resulting in cost and labour savings
 c) Better experimental planning and design of experiments
 d) This self-learning system can potentially help even in emerging areas such as predicting cell therapy outcome The process described in connection with FIG. 7 may be implemented in a computer program for predicting outcome a current process run for manufacturing a sample in a bioreactor. The computer program comprises instructions which, when executed on at least one processor, cause the at least one processor to carry out the method described in FIG. 7. The computer program may be stored on a computer-readable storage medium.

EXAMPLES

In the following mean results on test data over 100 75:25 CV Splits for different measures are presented.

In retrospective analysis on 20 experiments for 3 different output features (viable cell count, total cell count and product titre), we were able to achieve the accuracies listed in tables 1-3 below for look aheads between 1-5 days in advance. The metric used here for measurement is % points where error between actual and predicted features is $\Leftarrow 20\%$ Every step of the model improves accuracy, in line with the philosophy of the learning approach.

TABLE 1

| | Viable cell count | | | | |
|---|---|---|---|---|---|
| Model | 1 Day ahead | 2 Day ahead | 3 Day ahead | 4 Day ahead | 5 Day ahead |
| Base Model - BM | 57.78 | 59.83 | 59.10 | 59.26 | 56.68 |
| BM with learning - BMWL | 71.05 | 66.92 | 61.83 | 61.55 | 60.07 |
| BMWL + Error Corr. - BMWL(+EC) | 77.79 | 70.68 | 64.39 | 62.07 | 60.22 |
| BMWL(+EC) + Covariates - "step 77" | 77.43 | 70.63 | 64.25 | 62.62 | 60.34 |

TABLE 2

Total cell count

| Model | 1 Day ahead | 2 Day ahead | 3 Day ahead | 4 Day ahead | 5 Day ahead |
|---|---|---|---|---|---|
| Base Model - BM | 63.45 | 63.34 | 65.77 | 64.56 | 63.91 |
| BM with learning - BMWL | 73.92 | 69.97 | 67.31 | 67.15 | 64.66 |
| BMWL + Error Corr. - BMWL(+EC) | 79.62 | 72.16 | 67.91 | 65.80 | 64.86 |
| BMWL(+EC) + Covariates - "step 77" | 78.76 | 71.50 | 68.16 | 66.34 | 65.37 |

TABLE 2

Product titre

| Model | 1 Day ahead | 2 Day ahead | 3 Day ahead | 4 Day ahead | 5 Day ahead |
|---|---|---|---|---|---|
| Base Model - BM | 42.63 | 41.94 | 42.06 | 42.59 | 42.71 |
| BM with learning - BMWL | 55.62 | 47.04 | 43.92 | 41.75 | 39.56 |
| BMWL + Error Corr. - BMWL(+EC) | 57.38 | 49.83 | 47.19 | 41.54 | 39.79 |
| BMWL(+EC) + Covariates - "step 77" | 57.33 | 49.80 | 47.20 | 41.25 | 40.34 |

The method for predicting forecasts for a feature in a process used for manufacturing a sample in a bioreactor during a process run may be expressed as follow. Values related to the feature is continuously measured during a current process run, and the method comprises:

creating 74 a model for the current process run based on a selection of historic data;

after a time period, selecting 75 best fitting historic data related to the current process run, and updating the model based on the best fitting historic data; and revising 76 forecasts from updated model based on calculated errors between measured values and the updated model.

According to some embodiments, the method further comprising performing residual error correction 77 on the revised forecasts using metabolite information.

According to some embodiments the method further comprising setting 71 a set of conditions for the model, and obtaining 72 an amount of historic data from previous process runs to form the selection of historic data used to create the model.

According to some embodiments, the method further comprises controlling 73a if the amount of historic data obtained from previous runs is in a predetermined interval, and updating 73b conditions for the model if the amount of historic data is outside the predetermined interval and repeat the step of obtaining 72 an amount of historic data, or proceed to the step of creating 74 a model if the amount of historic data is within the predetermined interval.

According to some embodiments, the predetermined interval is selected to be historic data from at least ten previous process runs.

According to some embodiments, the predetermined interval is selected to be historic data from not more than one hundred previous process runs.

According to some embodiments, the method further comprises storing data from the current process run as historic data for future runs.

As mentioned above, the evaluation of data from bioprocesses is normally performed off-line and post-run, and not done as a comparison to the expected outcome. In order to provide an improved process, the following is implemented:

connect all data-generating sources in the bioprocess (as explained in more detail below).

establish a process model that represents both the "cell" (metabolism, proliferation, product formation, etc.) and the physical environment (mass transfer (e.g. oxygen), shear, mixing, etc.) The model will be build up from a limited set of equations. The first process runs will be used to determine model constants and the model will "self-learn/adapt" during consecutive process runs.

The model will be used together with on-line data to accomplish an on-line evaluation of the process, to construct soft-sensors, i.e. sensors that are implemented in algorithms using measured data from the system, which are used to improve process control. The overall aim is to both leverage all data and knowledge available, detect deviations at an early stage and to tighten the process controls.

The concept is illustrated in connection with FIGS. 9a-9b.

Figure 9A:
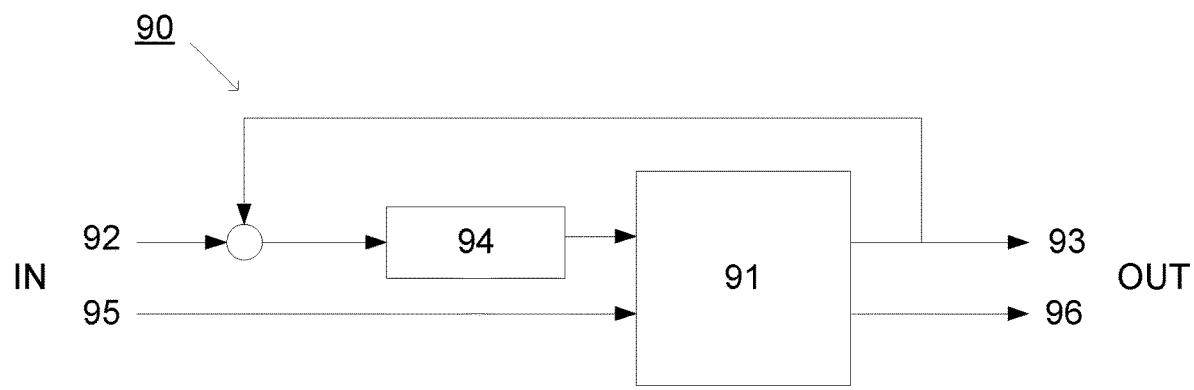
FIGS. 9a-9b illustrate a traditional, and a model based, bioprocess control and data evaluation, respectively.

FIG. 9a illustrates a traditional system setup 90 for bioprocess control and data evaluation. This may be used for a parameter related to the cell, e.g. pH, that is produced in a process 91. A set point 92, e.g. pH=7.0, and a measured parameter value 93 (after the process 91), e.g. pH=7.6, is compared with the set point and the difference, in this example pH=0.6, is used as an input to a controller 94. The controller 94 will cause a change of the parameter measured in the process by an addition 95 (in this example $CO_2$ or Base addition) to affect the measured parameter to achieve a desired difference between the set point and the measured value. The output 96 from the process is a sample for further processing in downstream processes and features, e.g. biomass concentration is measured on the sample.

Figure 9B:
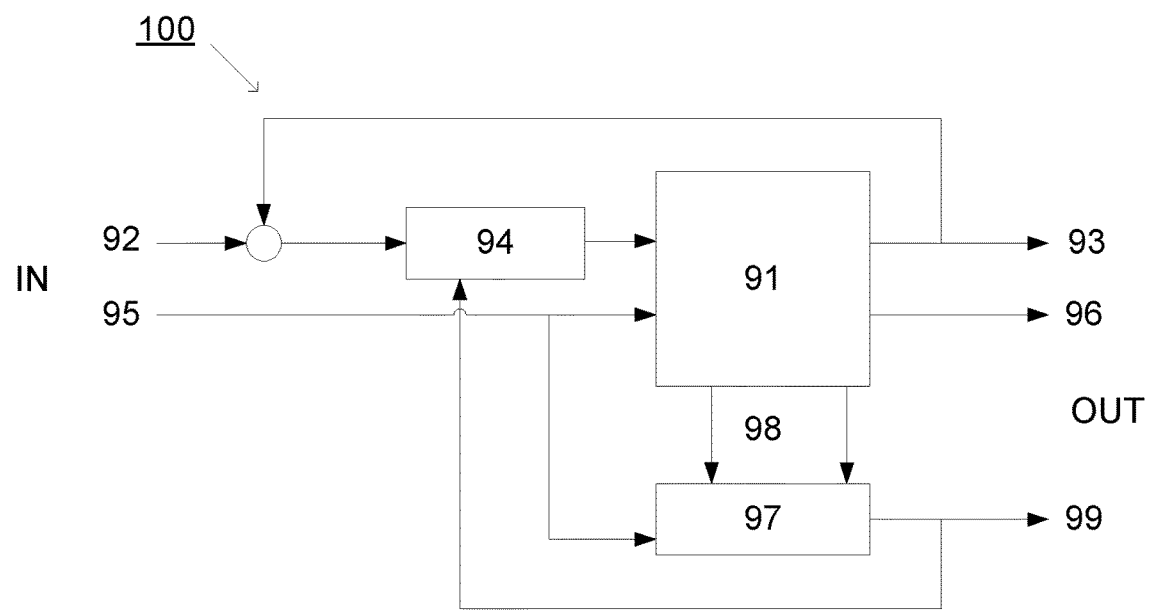

FIG. 9b illustrates an improved system setup 100 for model based control and data evaluation. This may be used to further improved the prediction of the outcome from the process. In addition to the features described in connection with FIG. 9a, the improved system setup 100 further comprises a unit 97 for creating a process model. Inputs from the addition 95 as well as model parameter estimations 98, are used to estimate at least one selected parameter 99 (Viable Cell Density (VCD), viability, titer (product concentration), concentration of metabolites, partial pressure of carbon dioxide ($pCO_2$), buffer capacity, PID parameters, oxygen mass transfer coefficient ($k_La$) cell specific rates, concentration of lactic acid, etc.)

The value of the at least one selected parameter is fed back to the controller 94 and used to control the process 91. Each parameter is indicative of a benefit for the user of the system, and provide a soft sensing.

When VCD or viability is estimated by the model, the harvest time may be estimated. When titer, [metabolites] or $pCO_2$ is estimated by the model, sampling frequency may be decreased. When $pCO_2$, buffer capacity, PID parameters or $K_La$ is estimated, control of the process may be improved and when cell specific rates are estimated On-line data evaluation may be performed.

The advantage with the system set-up described in connection with FIGS. 9a and 9b is that tighter and more robust results from the process is achieved. This will lead to more predictable product quality, which in turn means that the number of tests to establish a good quality product is reduced.

Normally several bioreactors are used to produce samples for downstream capture processes in a chromatography system. The amount of sample produced from the bioreactors has to be adapted to match the capacity of the downstream capture processes. This means that the downstream process may influence the input to the controller 94 and/or when building the model in the unit 97.

The invention claimed is:

1. A method for predicting outcome of a process used for manufacturing a sample in a bioreactor, the process belonging to a multi-level knowledge tree, wherein the method comprises:
   selecting a process model based on the multi-level knowledge tree, wherein each level of the knowledge tree corresponds to a category associated with a type of process;
   accessing historic data related to past process runs for manufacturing the sample;
   accessing current data obtained from a current process run of the process, wherein the obtained current data, which is based on the selected process model, comprises: process strategy data, bioreactor instrument data, data from online sensors and/or data from offline sensors;
   subselecting historic data of previous process runs similar to the current process run from the accessed historic data;
   predicting an outcome of at least one selected parameter selected from cell viability, cell count, product titre, and product quality of the current process run for manufacturing the sample based on the subselected historic data and current data;
   automatically determining an updated model for predicting outcomes of future process runs, wherein the updated model is determined based at least in part on:
      the process model based on the multi-level knowledge tree; and
      additional data from the current process run; and
   applying the updated model to future process runs of other samples.

2. The method according to claim 1, wherein the method further comprises consolidating historic data, current data and data related to the process model in a database.

3. The method according to claim 1, wherein obtaining current data further comprises:
   selecting parameters based on the base model used, and
   reading data of selected parameters.

4. The method according to claim 1, wherein the method further comprises handling of missing data in the current data obtained from the current process run.

5. The method according to claim 4, wherein handling of missing data further comprises:
   replacing missing data values with imputed values, or
   removing data with missing data values.

6. The method according to claim 1, wherein the method further comprises adapting the process model in real-time based on the current data.

7. The method according to claim 1, wherein the updated model is determined in response to completion of the current process run.

8. The method according to claim 6, wherein the process used in the current process run is determined to belong to a new category and the step of adapting the process run further comprises:
   assigning the process to the new category; and
   storing the process model as a new process model.

9. The method according to claim 1, wherein the step of predicting the outcome of at least one selected parameter further comprises:
   predicting a forecast of the at least one parameter; and/or
   predicting a forecast of anomalies; and/or
   determining and recommending actions to obtain improved conditions for the current process run.

10. A non-transitory computer-readable storage medium carrying a computer program predicting outcome of a current process run for manufacturing a sample in a bioreactor according to claim 1.

11. A method for modelling of a process used for manufacturing a sample in a bioreactor, the process belonging to a multi-level knowledge tree, wherein the method comprises:
   selecting a process model based on the multi-level knowledge tree, wherein each level of the knowledge tree corresponds to a category associated with a type of process;
   accessing historic data related to past process runs for manufacturing the sample;
   accessing current data obtained from a current process run of the process, wherein the current data, which is based on the selected process model, comprises: process strategy data, bioreactor instrument data, data from online sensors and/or data from offline sensors;
   monitoring at least one parameter selected from cell viability, cell count, product titre, and product quality of the current process run for manufacturing the sample;
   subselecting historic data of previous process runs similar to the current process run from the accessed historic data;
   automatically determining an updated model for predicting outcomes of future process runs, wherein the predicted outcome of future process runs comprises a prediction of the at least one parameter, and wherein the updated model is determined based at least in part on:
      the process model based on the multi-level knowledge tree; and
      additional data from the current process run; and
   applying the updated model to future process runs of other samples.

12. The method according to claim 11, wherein the method further comprises consolidating historic data, current data and data related to the process model in a database.

13. The method according to claim 11, wherein obtaining current data further comprises:
   selecting parameters based on the base model used, and
   reading data of selected parameters.

14. The method according to claim 11, wherein the method further comprises handling of missing data in the current data obtained from the current process run.

15. The method according to claim 14, wherein handling of missing data further comprises:
   replacing missing data values with imputed values, or
   removing data with missing data values.

16. The method according to claim 11, wherein the step of adapting the process model further comprises updating the process model for the category.

17. The method according to claim 11, wherein the process used in the current process run is determined to belong to a new category and the step of adapting the process model further comprises creating a new process model by:
   assigning the process to the new category; and
   storing the process model as a new process model.

18. A non-transitory computer-readable storage medium carrying a computer program for modelling of a process used for manufacturing a sample in a bioreactor according to claim 11.

19. A control system for controlling a process used for manufacturing a sample in a bioreactor, the process belonging to a multi-level knowledge tree, wherein the control system is configured to model the process and is further configured to:
  select a process model based on the multi-level knowledge tree, wherein each level of the knowledge tree corresponds to a category associated with a type of process;
  access historic data related to past process runs for manufacturing the sample;
  access current data obtained from a current process run of the process, wherein the obtained data, which is based on the selected process model, comprises: process strategy data, bioreactor instrument data, data from online sensors and/or data from offline sensors;
  subselect historic data of previous process runs similar to the current process run from the accessed historic data;
  predict an outcome of at least one selected parameter selected from cell viability, cell count, product titre, and product quality of the current process run for manufacturing the sample;
  control the process used for manufacturing the sample in a bioreactor based on the predicted outcome of the at least one selected parameter of the current process run;
  automatically determine an updated model for predicting outcomes of future process runs, wherein the updated model is determined based at least in part on:
    the process model based on the multi-level knowledge tree; and
    additional data from the current process run; and
  applying the updated model to future process runs of other samples.

20. The control system according to claim 19, wherein the sample is introduced into a separating system configured to purify the sample, and the control system is further configured to access data from the separating system and to improve the prediction based on the data from the separating system.

21. The control system according to claim 19, wherein the control system is configured to have access to a database with consolidated data comprising historic data, current data and data related to the process model.

22. A method for predicting forecasts for a feature in a process used for manufacturing a sample in a bioreactor during a process run, the process belonging to a multi-level knowledge tree, wherein each level of the knowledge-tree corresponds to a category associated with a type of process, values related to the feature being continuously measured during a current process run, wherein the method comprises:
  creating a model for the current process run based on a selection of historic data;
  after a time period during the current process run, automatically selecting best fitting historic data related to the values related to the feature being continuously measured during the current process run by subselecting historic data of previous process runs similar to the current process run, and updating the model to produce an updated model, wherein the updated model is determined based on the best fitting historic data and the model;
  revising forecasts during the current process run of at least one process parameter selected from cell viability, cell count, product titre, and product quality from the updated model based on calculated errors between measured values and the updated model; and
  applying the updated model for future process runs of other samples.

23. The method according to claim 22, wherein the method further comprises:
  performing residual error correction on the revised forecasts using metabolite information.

24. The method according to claim 22, further comprising:
  setting a set of conditions for the model, and
  obtaining an amount of historic data from previous process runs to form the selection of historic data used to create the model.

25. The method according to claim 24, wherein the method further comprises:
  controlling if the amount of historic data obtained from previous runs is in a predetermined interval, and
  updating conditions for the model if the amount of historic data is outside the predetermined interval and repeat the step of obtaining an amount of historic data, or proceed to the step of creating a model if the amount of historic data is within the predetermined interval.

26. The method according to claim 25, wherein the predetermined interval is selected to be historic data from at least ten previous process runs.

27. The method according to claim 25, wherein the predetermined interval is selected to be historic data from not more than one hundred previous process runs.

28. The method according to claim 22, wherein the method further comprises:
  storing data from the current process run as historic data for future runs.

29. The method according to claim 1, wherein the at least one process parameter is cell viability or cell count.

30. The method according to claim 11, wherein the at least one process parameter is cell viability or cell count.

31. The control system according to claim 19, wherein the at least one process parameter is cell viability or cell count.

32. The method according to claim 22, wherein the at least one process parameter is cell viability or cell count.

* * * * *